United States Patent
Aydinoglu

(10) Patent No.: US 8,940,324 B2
(45) Date of Patent: Jan. 27, 2015

(54) OCTENIDINE COMPOSITION

(75) Inventor: Ahmet Melih Aydinoglu, Ankara (TR)

(73) Assignee: Artan Holding AG, Triesen (LI)

( * ) Notice: Subject to any disclaimer, the term of this patent is extended or adjusted under 35 U.S.C. 154(b) by 506 days.

(21) Appl. No.: 13/128,266

(22) PCT Filed: Nov. 13, 2009

(86) PCT No.: PCT/EP2009/065111
§ 371 (c)(1),
(2), (4) Date: May 9, 2011

(87) PCT Pub. No.: WO2010/055122
PCT Pub. Date: May 20, 2010

(65) Prior Publication Data
US 2011/0217360 A1    Sep. 8, 2011

(30) Foreign Application Priority Data
Nov. 14, 2008  (EP) ..................... 08450183

(51) Int. Cl.
*A61K 31/444*  (2006.01)
*A61K 9/00*    (2006.01)
(Continued)

(52) U.S. Cl.
CPC .............. *A61K 9/0014* (2013.01); *A61K 9/0034* (2013.01); *A61K 47/26* (2013.01); *A61Q 17/005* (2013.01); *A61K 47/34* (2013.01); *A61K 8/4926* (2013.01); *A61K 8/345* (2013.01)
USPC .......................................... 424/445; 514/332

(58) Field of Classification Search
None
See application file for complete search history.

(56) References Cited

U.S. PATENT DOCUMENTS

| 4,420,484 A | 12/1983 | Gorman et al. |
| 5,177,065 A | 1/1993 | Silvetti, Sr. et al. |

(Continued)

FOREIGN PATENT DOCUMENTS

| DE | 196 47 892 A1 | 6/1998 |
| DE | 10 2004 052308 B4 | 4/2006 |

(Continued)

OTHER PUBLICATIONS

"Inhibition of intergeneric coaggregation among oral bacteria by cetylpryridium chloride, chlorhexidine digluconate and octenidine dihydrochloride," Smith, R., et al. J. Periodont. Res. 26: 422-428 (1991).*

(Continued)

*Primary Examiner* — Robert T Crow
*Assistant Examiner* — Daniel F Coughlin
(74) *Attorney, Agent, or Firm* — Oblon, Spivak, McClelland, Maier & Neustadt, L.L.P.

(57) ABSTRACT

The invention relates to octenidine or a pharmaceutical salt thereof, in particular octenidine dihydrochloride, which is intended for mutual therapeutic administration of the octenidine in solution with a polyalcohol of formula 1: $(H-C-OH)_a(HO-C-OH)_b(H-C-H)_c$, where a, b, c are whole numbers, where a+b is at least 2, preferably at least 3, c is selected from 0, 1 or a number from 2 to a+b, optionally in addition to one or more aldehyde groups provided that they form (cyclic) acetals with one of the hydroxy groups or one or more keto groups optionally as acetal with one of the hydroxy groups, optionally in addition to one or more carboxylic acid groups if the polyalcohol is a cyclic acetal or acetal, preferably with ring sizes of 5 to 7 atoms, or a polymer, polyether or polyester thereof, provided that the polyalcohol exists as a polymer, polyether or polyester with at least two units of formula 1 if a+b is 2 or 3. The invention also relates to kits containing these ingredients, and use thereof for treating infections and wounds.

11 Claims, 5 Drawing Sheets

Figure 1:
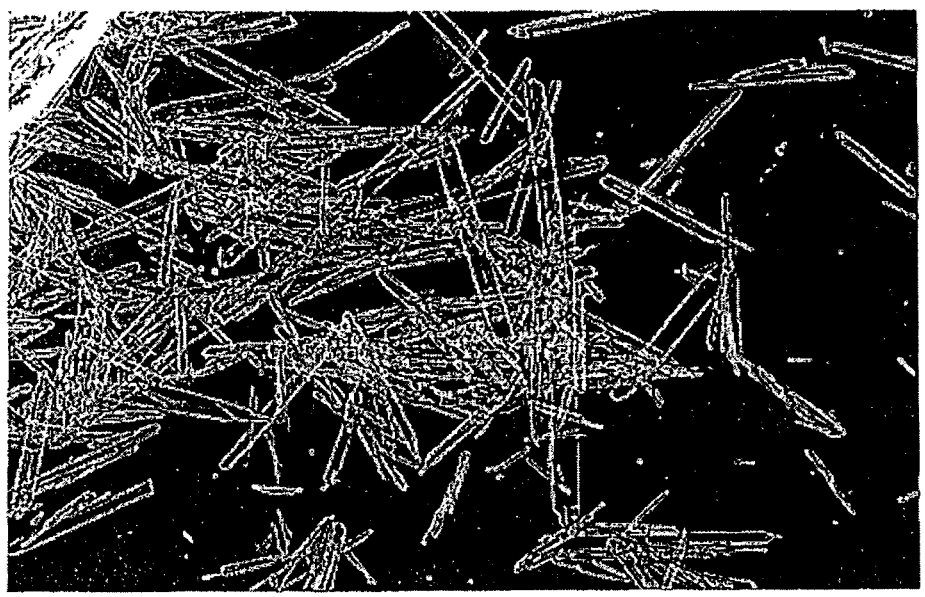

(51) Int. Cl.
*A61K 47/26* (2006.01)
*A61Q 17/00* (2006.01)
*A61K 47/34* (2006.01)
*A61K 8/49* (2006.01)
*A61K 8/34* (2006.01)

(56) References Cited

U.S. PATENT DOCUMENTS

| | | | | |
|---|---|---|---|---|
| 2001/0036963 | A1* | 11/2001 | Behrends et al. | 514/557 |
| 2006/0165612 | A1 | 7/2006 | Beilfuss et al. | |
| 2008/0142023 | A1 | 6/2008 | Schmid et al. | |
| 2008/0175801 | A1* | 7/2008 | Ramji | 424/53 |

FOREIGN PATENT DOCUMENTS

| | | | |
|---|---|---|---|
| EA | 200700777 A1 | 10/2007 | |
| EP | 0 411 315 A1 | 2/1991 | |
| EP | 1 683 416 A1 | 7/2006 | |
| EP | 1 683 417 A1 | 7/2006 | |
| ES | 2 304 519 T3 | 11/2004 | |
| ES | 2 309 790 T3 | 6/2007 | |
| FR | 2 907 683 A1 | 5/2008 | |
| JP | 2001505552 A | 4/2001 | |
| JP | 2001525877 A | 12/2001 | |
| JP | 2005517030 A | 6/2005 | |
| WO | WO 02/069874 A2 | 9/2002 | |
| WO | WO 03/067988 A1 | 8/2003 | |
| WO | WO 03/077941 A1 | 9/2003 | |
| WO | WO 2006039961 A1 | * 4/2006 | |
| WO | WO 2007/023066 A1 | 3/2007 | |
| WO | WO 2007/031519 A2 | 3/2007 | |
| WO | WO 2007/031520 A2 | 3/2007 | |

OTHER PUBLICATIONS

Notice of Opposition issued Sep. 24, 2012 in European Patent Application No. 2291185 with English language translation.
"Lösung zur Wund- und Schleimhautdesinfektion", Schülke & Mayr, Octenisept, Feb. 2007, pp. 1-8.
Alex Kramer, et al., "Influence of the Antiseptic Agents Polyhexanide and Octenidine on FL Cells and on Healing of Experimental Superficial Aseptic Wounds in Piglets", Skin Pharmacology and Physiology, vol. 17, XP 9113654A, 2004, pp. 141-146.
Office Action issued Jun. 18, 2013, in Colombian Patent Application No. PCT/EP2009/065111 submitting English translation only.
International Search Report issued Jan. 14, 2010 in PCT/EP2009/065111.
Office Action issued Oct. 4, 2013 in Cuban Patent Application No. 2011-0105 (with English language translation).
Office Action issued Sep. 30, 2013 in European Patent Application No. 09756292.0.
Deutsche Übersetzung des Einspruchsschriftsatzes (German translation of the Notice of Opposition) issued Sep. 24, 2012 in European Patent Application No. 09756292.0 (with English language translation).
Karin Hehenberger, at al., "Inhibited proliferation of fibroblasts derived from chronic diabetic wounds and normal dermal fibroblasts treated with high glucose is associated with increased formation of L-lactate" Wound Repair and Regeneration, vol. 6 No. 2, 1998 (submitting English Summary only).
Jaakko Kivisaari, et al., "Energy Metabolism of Experimental Wounds at Various Oxygen Environments" Oxygen and Healing, Ann. Surg., vol. 181 No. 6, Jun. 1975, pp. 823-828.
E. Patchen Dellinger, "Preventing Surgical-Site Infections: The Importance of Timing and Glucose Control" Infection Control and Hospital Epidemiology, vol. 22 No. 10, Oct. 2001, pp. 604-606.
Official Action issued Mar. 20, 2014, in Eurasian Patent Application No. 201100762, filed Nov. 13, 2009 (with English-language Translation).
Notice of Reasons for Rejection issued Jan. 7, 2014, in Japanese Patent Application No. 2011-536025, filed Nov. 13, 2009 (with English-language Translation).
Official Action issued Apr. 14, 2014, in Chilean Patent Application No. 1081-11, with English-language Translation.
A. Kramer, et al., "Influence of the Antiseptic Agents Polyhexanide and Octenidine on FL Cells and on Healing of Experimental Superficial Aseptic Wounds in Piglets" Skin Pharmacology and Physiology, Skin Pharmacol Physiol 2004;17 (pp. 141-146).
Office Action issued by Eurasian Patent Office in application No. 201100762, dated Oct. 29, 2014.

\* cited by examiner

O: Octenisept
O+N: Octenisept and NaCl
O+N+G: Octenisept and NaCl and glucose
1: Glycerol phosphate
2: Fructose-1-6-*bis*-phosphate
3: Glucose-1-phosphate
4: Glucosamine
5: D-Sorbitol
6: Ribose
7: Fructose
8: Glycolaldehyde One-Sample T-Test: significant change compared to Octenisept + glucose (=1) (*=p<0,05; **=p<0,01)

OCTENIDINE COMPOSITION

The present invention relates to the field of disinfecting and antiseptic formulations as well as their use.

Octenidine dihydrochloride is a microbicide agent which is used in particular in antiseptic agents for the skin, the mucous membranes and wounds. It is sold under the brand name Octenisept®. Due to its broad spectrum of activity on the one hand and its good tolerance on the other this active agent increasingly gains importance in the field of antisepsis and has already replaced conventional antiseptic agents like chlorhexidine, triclosan and PVP-I in several areas of indication.

Octenidine is strongly adsorbed by negative cell surfaces. There it reacts with anionic polysaccharides of the microbial cell wall and phospholipids of the cell membrane, interferes with the enzymatic systems, disturbs cell functions and leads to the leakage of the plasma membrane. As a result the function of the mitochondria is disturbed. Studies show a strong adherence to lipid components in cell membranes (e.g. cardiolipin) which explains the high anti-microbial effect while at the same time it is well tolerated by the human epithelia and traumatic tissue. With an exposure time of 30 min. octenidine in the dilution of 22 or 17 mg/l (=0.0022% and 0.0017% respectively) is effective against *E. coli* and *S. aureus* (Kramer A., Müller G., Octenidindihydrochlorid, IN: *Wallhäußers Praxis der Sterilisation, Desinfektion, Antiseptik and Konservierung*, Stuttgart, Thieme, 2007).

Octenidine and octenidine dihydrochloride and its derivatives are described in U.S. Pat. Nos. 4,206,215 and 4,442,125 as anti-microbial substances.

DE 3 925 540 C1 relates to an aqueous antiseptic composition comprising octenidine as well as phenoxyethanol and/or phenoxypropanol which are used as solubilizer.

DE 10 2004 052 308 A1 and WO 2006/039961 relate to lozenges comprising octenidine which is provided in a solid sugar matrix. This matrix is a solid sugar mass with about 70-99.95% w/w which serves as a carrier and masks the bitter taste of octenidine.

WO 2007/023066 A1 relates to an octenidine dihydrochloride solution and a mono- or bivalent alcohol or glycerin. These alcohols are considered as an alternative to conventional phenoxyethanol or phenoxypropanol of earlier octenidine dihydrochloride preparations.

WO 2007/031519 A2 relates to octenidine dihydrochloride preparations in the form of encapsulating liposomes. The cytotoxicity of octenidine is supposed to be reduced by the use of phospholipid liposomes.

EP 1 683 416 A relates to the addition of alcohol to octenidine solutions. Sorbitol or glycerin was added to sample formulations.

EP 1 638 417 A relates to octenidine formulations comprising specific glycerin ethers. Sample formulations show glycerin or sodium gluconate as an additive.

U.S. Pat. No. 4,420,484 A relates to solutions of antimicrobial amino and ammonium compounds. Octenidine in a formulation together with PEG is also shown.

WO 2007/023066 A relates to solutions of octenidine dihydrochloride for the disinfection of wounds and mucous membranes, wherein it was one object to replace additives as for example phenoxyethanol with other alcohols. For instance it is recommended to add for example pentane-1,2-diol. Glycerin is mentioned as an additive.

Kramer et al., *Skin Pharmacology and Physiology*, 17 (2004): 141-146 relates to a study concerned with the comparison of the antiseptic potential of octenidine and polyhexanide. The result showed that octenidine was slightly less effective than polyhexanide and that this reduction could not be traced to the addition of phenoxyethanol which is present in Octenisept®.

US 2001/03693 A1 describes octenidine formulations with monovalent alcohols.

Despite the advantages of octenidine it would be desirable to obtain a preparation which has an improved effect in particular when it comes to the therapeutic use in the field of wound and mucous membrane antisepsis.

Therefore the present invention in one aspect relates to octenidine or a pharmaceutical salt thereof, in particular octenidine dihydrochloride, intended for combined therapeutic administration of the octenidine in solution with a polyalcohol of formula 1: $(H-C-OH)_a(HO-C-OH)_b(H-C-H)_c$, wherein a, b, c are integers, wherein a+b is at least 2, preferably at least 3, c is selected from 0, 1 or a number in the range of 2 to a+b, in addition with one or more aldehyde groups provided that they form (cyclic) hemiacetals or acetals with one of the hydroxy groups and/or one or more keto groups optionally as acetal (or ketal) with one of the hydroxy groups, optionally in addition to one or more carboxylic acid groups if the polyalcohol is a cyclic hemiacetal or acetal, preferably with ring sizes of 5 to 7 atoms, or a polymer, polyether or polyester thereof, provided that the polyalcohol exists as a polymer, polyether or polyester with at least two units of formula 1 if a+b is 2 or 3. In one particularly preferred aspect the present invention relates to a pharmaceutical composition with octenidine and glucose as a mixture or as separate components in a kit for combined administration in solution.

Preferably the present invention in one aspect relates to a pharmaceutical composition comprising a solution of octenidine, preferably octenidine dihydrochloride, or one of its pharmaceutically acceptable salts and glucose with a glucose concentration of between 0.01% to 12% (w/v), preferably between 0.1% to 10%, more preferably between 0.5% to 7.5%, most preferably between 2.5% to 5%, and an octenidine concentration of between 0.0001% to 5% (w/w), preferably between 0.001% to 0.1%, more preferably between 0.002% to 0.05%, optionally in combination with a carrier. Particular and further objects of the invention are defined in the claims.

Octenidine is a highly effective bacteriostatic/bactericidal agent which is frequently utilized for wound cleaning as well as preoperatively for the disinfection of the operation area, in particular in form of dihydrochloride salt. So far it is mostly used as an aqueous solution with a concentration of 0.1% (w/v) or as a 1:1 dilution with $NaCl_{physiol}$. However, the excellent inhibition of prokaryotes also has certain disadvantages for the growth of eucaryotic cells which have to proliferate and differentiate for correct wound healing in order to form a well adherent and tight wound closure. The stability of the cellular closure is dependent on the formation of molecular interactions of the tissue matrix with the cell surface molecules.

According to the invention it was demonstrated that the use of $NaCl_{phisiol}$ causes a precipitation in the case of Octenisept® which diminishes the effectiveness. It could further be demonstrated that this disadvantage can be avoided by adding polyalcohols, in particular glucose. Used in certain concentrations this formulation promotes the enhanced formation of cell-matrix-interactions, subsequently called cell adhesion, which was measured in cultivated fibroblastoid cells with a cell adhesion assay. With this measurement method the effect of the inventive composition was measured and the optimal polyalcohol concentration, in particular glucose concentration, verified.

The interaction of octenidine and bacteria is a factor for its effectiveness. According to previous findings the negatively charged bacteria surface mainly seems to be responsible for the attachment of positively charged octenidine. If one administers, like it is frequently done, Octenisept® in a dilution of 1:1 with physiological sodium chloride solution it is assumed —without being limited to one single theory—that the mixed hydrate shell consisting of NaCl and the dipole water which forms around the octenidine molecule leads to a reduction of the effective positive charge and subsequently to an impairment of the interaction with the bacterial wall. According to the invention it was observed that the addition of polyalcohols, in particular glucose, improves the wound healing without impairing the anti-septic effectiveness, yet actually enhancing it.

It was shown in the examples that the use of a dilution with NaCl leads to the formation of a sediment. In this sediment octenidine is found as an inactive crystalline foreign substance which masks the availability of the bactericidal effect and which will unwantedly interact with the wound healing since it furthermore exerts a mechanic irritation in wounds. This interaction can be prevented through dilutions with uncharged carbohydrates as for example with 5% glucose solution.

Octenidine primarily acts anti-bacterially due to its affinity to bacterial surfaces. In addition octenidine has a disinfecting/antimicrobial effect against fungi and viruses which can fully develop if administered together with a polyalcohol according to the invention. The polyalcohol furthermore supports a stabilization of the cell structure which is desired for wound healing, which becomes obvious through the cell adhesion test demonstrated in the examples.

On the one hand the compositions according to the invention show the effectiveness in relation to the improvement of the cell adhesion which was experimentally proven to be particularly preferred in the range of 1 g/l to 25 g/l (0.1% to 2.5%). On the other hand when using hypotonic Octenisept® there exists an increased occurrence of wound pain due to the effect of the receptors and ion canals involved in the nociception. Through the use of the composition according to the invention for the proposed mutual administration in case of wounds and sensitive mucous membranes with almost isotonic solutions (corresponding to about 5% glucose) or in some cases also slightly hypotonic solutions (corresponding to 2.5% glucose) the negative effect on the nociception is reduced or eliminated. Hence freedom from pain and a substantial improvement of the treatment is achieved and in particular also in a consecutive reaction, in case of applications like on the peritoneum, a fluid shift is prevented.

Therefore, according to the present invention octenidine is provided together with a polyalcohol for mutual administration. This polyalcohol preferably comprises a primary structure of the formula 1: $(H-C-OH)_a(HO-C-OH)_b(H-C-H)_c$. Preferably a+b are at least 2, at least 3, at least 4, at least 5, at least 6 or also at least 7. Taken alone a is preferably 0, 1, 2, 3, 4, 5, 6 or also at least 7. In combination or independently b therefore can be selected from 0, 1, 2, 3, 4, 5, 6 or at least 7. The definitions of a and b determine the number of hydroxyl groups which are important according to the invention. It is particularly preferred that the polyalcohols have at least 4, preferably at least 5, 6, 7 or also at least 8 hydroxyl groups. In case of a+b=2 or 3, in further special cases also if a+b=4 or 5, it is therefore preferably provided that the structure of the above formula 1 is given as a polymer, in particular polycondensate, polyether or polyester. Of course also bigger structural elements of the formula 1 can be provided as polymers, polycondensates, polyethers or polyesters, wherein a connective O or OC(O) of the polyethers or polyesters was not mentioned in the formula above and is possible as an additional connective structural element. The term "poly" in this connection has to be understood as specification of the above structural elements which can occur at least twofold, preferably threefold, more preferably fourfold, specifically preferred fivefold or also at least six-fold. In case of polymers up to 5000, up to 4000, up to 3000, up to 2000, up to 1000, up to 800, up to 500 or up to 300 elements of the formula 1 can be provided.

Therein the elements can be built uniformly or homogenously from the same basic element or heterogenously from mixtures thereof. Preferably carbohydrate polymers from sugar monomers or derivatives thereof are heterogenous.

The polyalcohols according to the invention can additionally be provided with one or more aldehyde groups provided that they form (cyclic) hemiacetals or acetals with one of the hydroxy groups or one or more keto groups, optionally as an acetal with an hydroxy group. The formation of aldehydes as acetals is particularly preferred since aldehyde groups potentially act toxic due to their high reactivity. Therefore it is specifically preferred that the aldehyde exists in balance with its acetal, preferably to at least 95%, in particular at least 98%, specifically preferred 99%, as acetal in balance to the open aldehyde structure under physiological conditions, in particular at 37° C. In case a keto group is provided it exists in also preferred embodiments to at least 95%, preferably at least 98%, at least 99% as acetal in balance with one of the hydroxy groups of the polyalcohols (intramolecularly) under physiological conditions, in particular at 37° C. Preferably the hemiacetals or acetals form intramolecular rings with 5, 6, 7, 8 or also 9 atoms. Preferably the polyalcohol, in particular in the form of an acetal, contains a glycoside.

Optionally the polyalcohol of the basic structure of the formula 1 can have a carboxylic acid group provided that the polyalcohol is a cyclic hemiacetal or acetal, preferably with ring sizes of 5 to 7 atoms. Although it was inventively established that acid groups are less effective together with octenidine it was shown on the basis of glucuronic acid for example that an enhanced effectiveness (compared to conventional Octenisept®) could nevertheless be recorded. Glucuronic acid is a carboxylic acid which exist analogously to glucose as a cyclic acetal with 6 atoms wherein the sixth carbon atom is oxidized to carboxylic acid.

In addition as to the purpose bound octenidine or the pharmaceutical salt thereof the present invention in a further aspect relates to a kit comprising a polyalcohol as defined above and octenidine or pharmaceutical salts thereof, in particular octenidine dihydrochloride, preferably intended for combined therapeutic administration in solution. Octenidine in particular or its salt can according to the kit be provided as dissolved octenidine. As an alternative or an addition the polyalcohol can already be dissolved. Such a solution makes a quick utilization of octenidine possible, in particular for disinfection.

In a further aspect the present invention relates to a pharmaceutical composition in form of a solution comprising a polyalcohol as defined above and octenidine or pharmaceutical salts thereof, in particular octenidine dihydrochloride. Also mixtures of the polyalcohol with octenidine as pharmaceutical compositions are disclosed. Solid mixtures can be provided in particular for later dissolution shortly before administration.

Preferably the polyalcohol according to the present invention is a carbohydrate with the chemical formula 2: $C_n(H_2O)_m$, wherein n is an integer of at least 3, preferably 4, 5, 6, 7, 8, 9, 10, 11 or at least 12 and m is an integer in the range of n−15% to n+15% (rounded integers), preferably n−1, n or n+1. here the rounding is done mathematically, i.e. decimal places of . . . , 5 are rounded up and . . . , 4999 are rounded down. Of course also these carbohydrates can be polymerized, in particular polycondensated, into soluble carbohydrate oligomers or carbohydrate polymers. In particular the ability to form solutions without turbidity caused by the polyalcohol is particularly preferred. Although in particularly preferred embodiments the preparation according to the present invention is provided as a gel, in particular a hydrogel, the polyalcohol according to the invention is not understood as a gel former, in particular since a gel former is not understood as a soluble substance but as a solvated semi-solid structure.

In particularly preferred embodiments the polyalcohol is uncharged. Although also slightly acid polyalcohols as for example the glucuronic acid are possible the best results are achieved with uncharged polyalcohols. If the polyalcohol is a weak acid the pKa value of the polyalcohol is preferably greater than 3, more preferably greater than 3.5, greater than 4, greater than 4.5 or greater than 5.

In particularly preferred embodiments the polyalcohol is a mono- or disaccharide or a deoxy- or mono-carboxylic acid derivative of a mono- or disaccharide. In further special embodiments the polyalcohol comprises an aldose or ketose, preferably an aldohexose, aldopentose, ketohexose or a ketopentose. Particularly preferred examples of the polyalcohols of the invention are glucose, galactose, fructose, fucose, maltose, ribose, deoxyribose, deoxyglucose, in particular 2-deoxyglucose, saccharose, lactose, glucuronic acid, dextrose, isomalt, malitol syrup, polyglucose, glucanes and fructooligosaccharides.

Preferably octenidine and the polyalcohol are dissolved in aqueous solutions, preferably in pure water. Optionally a little amount of alcohol can be provided as a solvent, e.g. ethanol, propanol or isobutanol. In such cases the alcohol concentration preferably is under 5%, under 3%, under 2% or under 1%.

Preferably the polyalcohol in solution for the administration with octenidine is provided at a concentration of at least 0.001%, at least 0.005% or at least 0.01%, preferably at least 0.025%, particularly preferred at least 0.1%, at least 0.5%, at least 1%, most preferred at least 2.5% (w/v). The concentration specification (w/v) in this case concerns a concentration of weight per volume. Preferably the maximum concentration of the polyalcohol in solution for the administration with octenidine is 12%, preferably 10%, in particular up to 7.5%, most preferred up to 5% (w/v).

In further particularly preferred embodiments octenidine in solution for the administration with the polyalcohol or in the mutual solution of the composition or in the kit has an octenidine concentration of at least 0.0001%, particularly preferred at least 0.001%, particularly preferred at least 0.002%, at least 0.005%, at least 0.01% or at least 0.05% (w/w). In further particularly preferred embodiments the octenidine concentration is up to 5%, up to 1%, up to 0.5% or up to 0.2% (w/w).

Although it was inventively determined that the polyalcohol according to the present invention can prevent a masking effect of salt, in particular NaCl, on octenidine it is preferred that the salt concentration, in particular the NaCl concentration, is at most 0.5% (w/v), preferably at most 0.1%, at most 0.05%, at most 0.01%, particularly preferred at most 0.005%, most preferred at most 0.001%.

In special embodiments the polyalcohol and/or the octenidine in the preparation of the purpose-bound octenidine of the kit or of the composition is provided in a carrier. The carrier is preferably selected from a gel, preferably a hydrogel, or a wound dressing or a swab, optionally impregnated with a solution containing the polyalcohol and/or octenidine. Further carriers comprise carriers for slow-release which release the active agent combination as a longer effective application delayed or slower. Such a preparation with a corresponding carrier is especially suitable for topical and quick administration.

The octenidine, the kit or the composition according to the present invention with octenidine and the polyalcohol for combined therapeutic administration is particularly intended for the treatment of wounds or burns, in particular relating to the skin, a mucous membrane, particularly the vagina, the abdominal cavity, of internal organs, in particular in case of surgical procedures or in order to prevent surgical procedures, or for the treatment and prevention of infections, in particular wound infections, preferably infections of burn wounds, particularly of the skin, a mucous membrane, particularly the vagina, of the abdominal cavity, of internal organs, in particular in case of surgical procedures or in order to prevent surgical procedures. In a further aspect the present invention relates to the polyalcohol, preferably glucose, intended to enhance the effectiveness of octenidine when used therapeutically; as well as octenidine or a pharmaceutical salt thereof, as for example octenidine dihydrochloride, intended for mutual therapeutic administration with the polyalcohol, preferably glucose.

The use of glucose 5% as an easy-handling, everywhere obtainable and easily predictable diluent makes it possible for the octenidine to bind to the bacterial surfaces with uninhibited affinity since the bacteriostatic effect is fully present and supports a stabilization of the cell structure which is desirable for wound healing as can be deduced from the cell adhesion tests.

In a further aspect the present invention relates to a kit comprising glucose and octenidine or a pharmaceutical salt thereof, in particular octenidine dihydrochloride. The inventive effect of improved wound healing occurs in particularly in case of combined administration of this kit. A kit in which glucose and octenidine are provided separately can also be provided. The components can be particularly intended for combined administration. Preferably either glucose or octenidine or both components are in solution. The use of dissolved glucose or octenidine, particularly preferred dissolved glucose as well as dissolved octenidine, allows for a quick administration for example through the mixing of both substances or both solutions and subsequent application.

The solution in which the kit or the pharmaceutical composition according to the present invention is provided preferably is an aqueous solution. In particular water can be provided as a pure solvent but also with little of other organic solvents as for example alcohols. Preferably the alcohol content of such a solution is less than 10%, in particular less than 5%, particularly preferred at most 2% or less than 1%.

The polyalcohol concentration, preferably glucose concentration, in a polyalcohol solution of the kit for administration with octenidine or a pharmaceutical composition in which both substances are already mixed preferably is at least 0.001%, at least 0.005% or at least 0.01%, particularly preferred at least 0.05% or at least 0.1%, specifically preferred at least 0.5%, at least 1% or at least 2.5% (all percentages given are w/v). Preferably the polyalcohol concentration, preferably the glucose concentration, is at most 30%, at most 20%, at most 10%, at most 8%, at most 5% (w/v). The preferred concentrations in the kit comprising a polyalcohol solution and an octenidine solution intended for mixing for example with a ratio of 1:1 are adequately increased for example they are doubled in case of a mixture ratio of 1:1, for example a polyalcohol concentration of 5-10% for the polyalcohol solution and an octenidine concentration of 0.004-1% for octenidine solutions are preferred the most.

The herein used concentration indication (w/v) stands for weight per volume. The concentration indication (w/w) which is also used herein stands for weight per total weight of the respective preparations or solutions.

Preferably the octenidine solution for mutual administration with glucose or the pharmaceutical composition comprising a solution of octenidine has an octenidine concentration of at least 0.0001% (w/w), preferably at least 0.001%, particularly preferred at least 0.002%, at least 0.005%, at least 0.01% or at least 0.05%. Preferably the maximum concentrations of octenidine are up to 10% (w/w), preferably up to 5%, up to 1%, particularly preferred up to 0.5%, specifically preferred up to 0.2%.

As already mentioned herein and also demonstrated with the examples a salt amount, in particular a high NaCl concentration, can for example under physiological conditions inhibit the effect of octenidine. Although glucose can prevent this inhibiting effect the NaCl concentration is limited in special embodiments of the present invention. Preferably the octenidine solution for administration with glucose or the pharmaceutical composition according to the invention comprises a salt concentration, in particular an NaCl concentration, of less than 0.1% (w/v), preferably less than 0.05% or less than 0.01%, particularly preferred less than 0.05%, mostly preferred less than 0.001%.

According to the kit of the present invention as well as to the pharmaceutical composition with octenidine and glucose the glucose and/or octenidine can be provided in a carrier. Preferably the carrier is a gel, in particular a hydrogel. A further possible carrier is a wound dressing or a swab optionally impregnated with a solution containing glucose and/or octenidine. Such a wound dressing or such a gel can be administered directly or by addition of the respective other component selected from glucose and/or octenidine. Further carriers comprise slow-release carriers as for example microcapsules which release the active agent combination as a longer effective administration time-delayed or slower. A gel or hydrogel can be produced with conventional gel formers as for example cellulose derivatives like hydroxy ethyl cellulose. Further possible carriers comprise emulsions, preferably oil in water or water in oil emulsions and liposomes. In particular it is preferred that the solutions according to the invention are provided sterile.

In general the present invention therefore relates to a pharmaceutical composition in form of a solution comprising glucose and octenidine, preferably like in the Octenisept® composition.

The kit according to the invention or the composition is particularly used for the manufacture of a medicament for therapeutic administration for the treatment of wounds or burns or for the treatment and prevention of infections, in particular of wound infections. Preferably the composition or the kit are used for the treatment of wounds, infections, in particular wound infections, burns of the skin, of a mucous membrane, in particular the vagina, of internal organs, the abdominal cavity, in particular in case of surgical procedures. The preparations according to the invention therefore constitute an especially useful remedy which can be used effectively as a disinfecting agent when it comes to surgical procedures.

The pharmaceutical composition or the glucose or octenidine solution of the kit according to the invention are particularly intended in case of physiological pH. The pH-value therefore can for example be between 5 and 9, preferably up to pH 8. Provided it is necessary the pH-value can be provided through suitable buffers as for example of organic acids like citric acid, acetic acid, fumaric acid or malic acid, as well as of inorganic acids as for example hydrochloric acid, phosphoric acid or sulfuric acid or their alkali metal salts or alkaline earth metal salts, in particular sodium, potassium, magnesium, calcium, or through buffers of pharmaceutically acceptable bases, for example NaOH.

In particular according to the invention the solution of octenidine or the complete pharmaceutical composition is a clear solution without precipitated octenidine. This solution as such can be provided in the carrier material of the present invention, for example in a gel or hydrogel or a wound dressing.

The present invention is further illustrated by the following non-limiting drawings and examples. In said drawings:

FIG. 1: Inverted microscopy image of precipitated octenidine crystals from an Octenisept®-NaCl-solution.

Figure 2A:
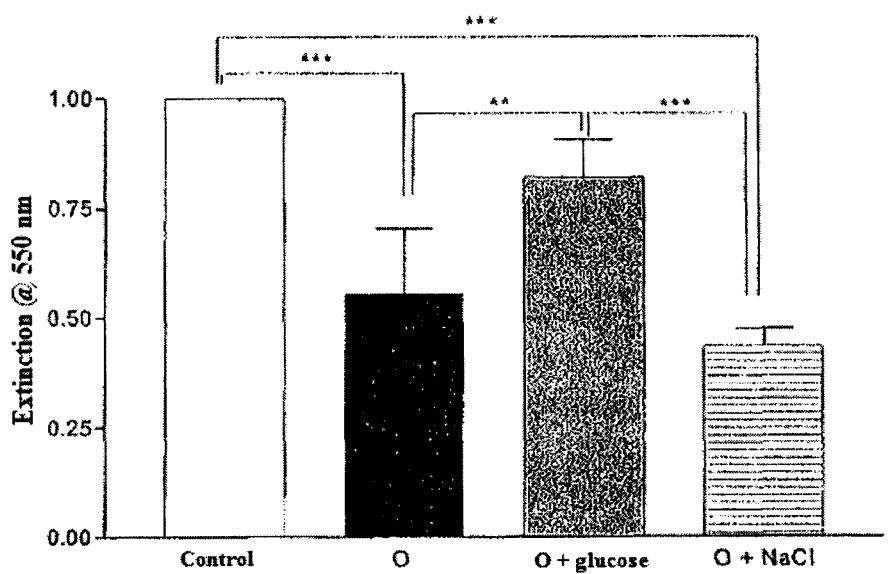
Figure 2B:
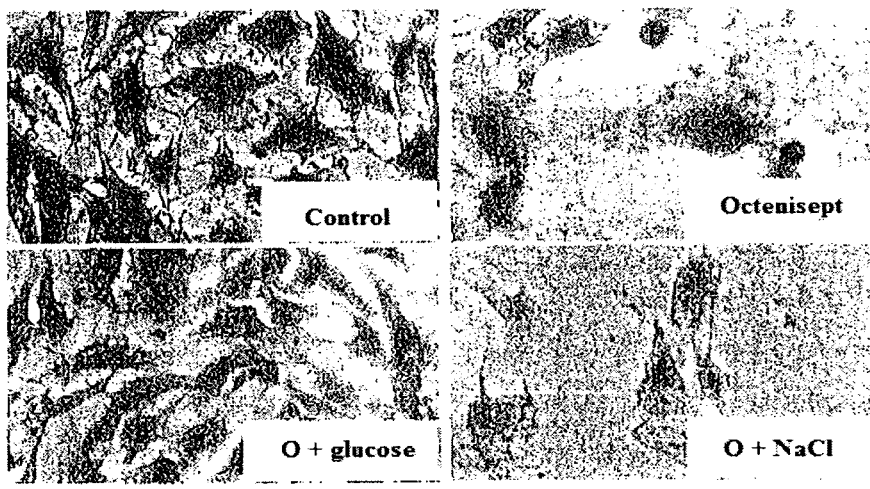

FIG. 2: Modification of the Octenisept® induced cell detachment through the addition of NaCl or glucose in the cell detachment assay with Methyl violet. a: graphic bar chart of the results: the bars represent the mean value±standard deviation of four independent experiments. b: photography of the cell layers.

Figure 3A:
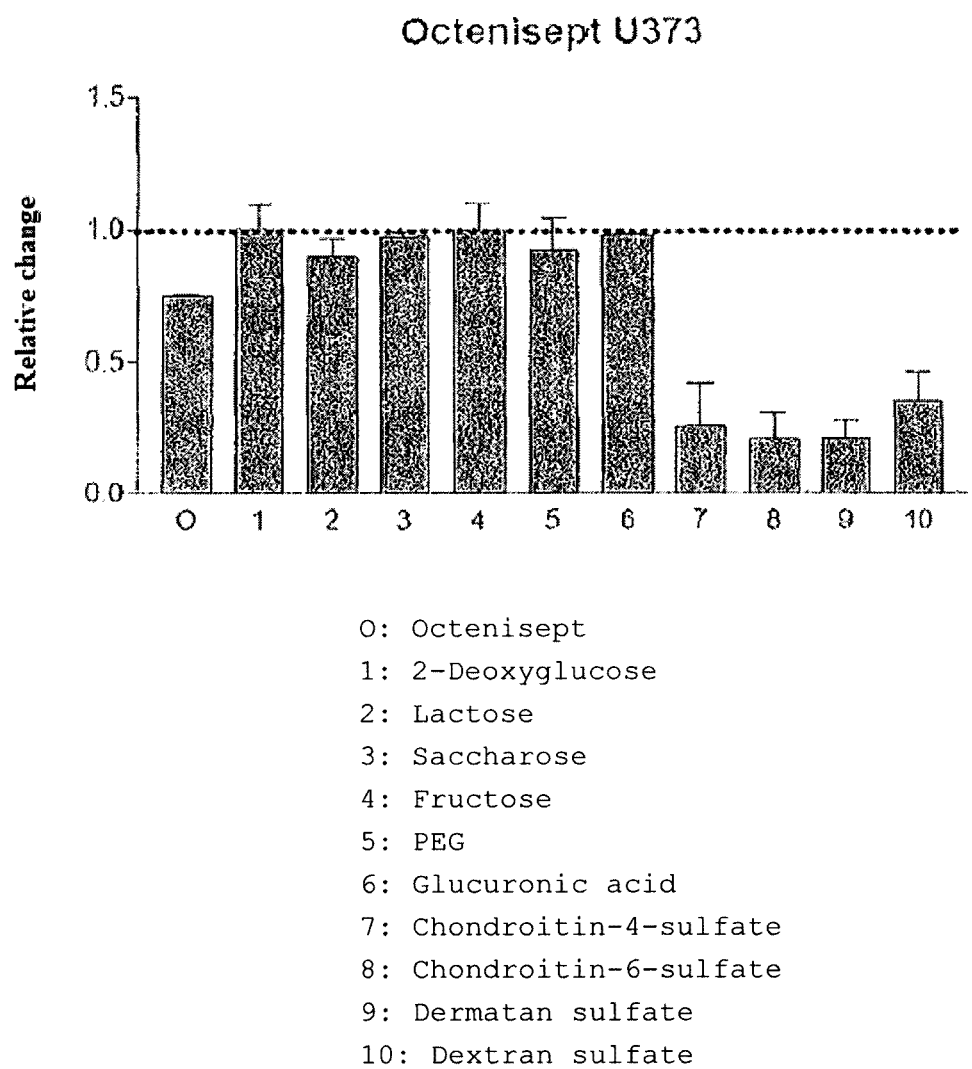
Figure 3B:
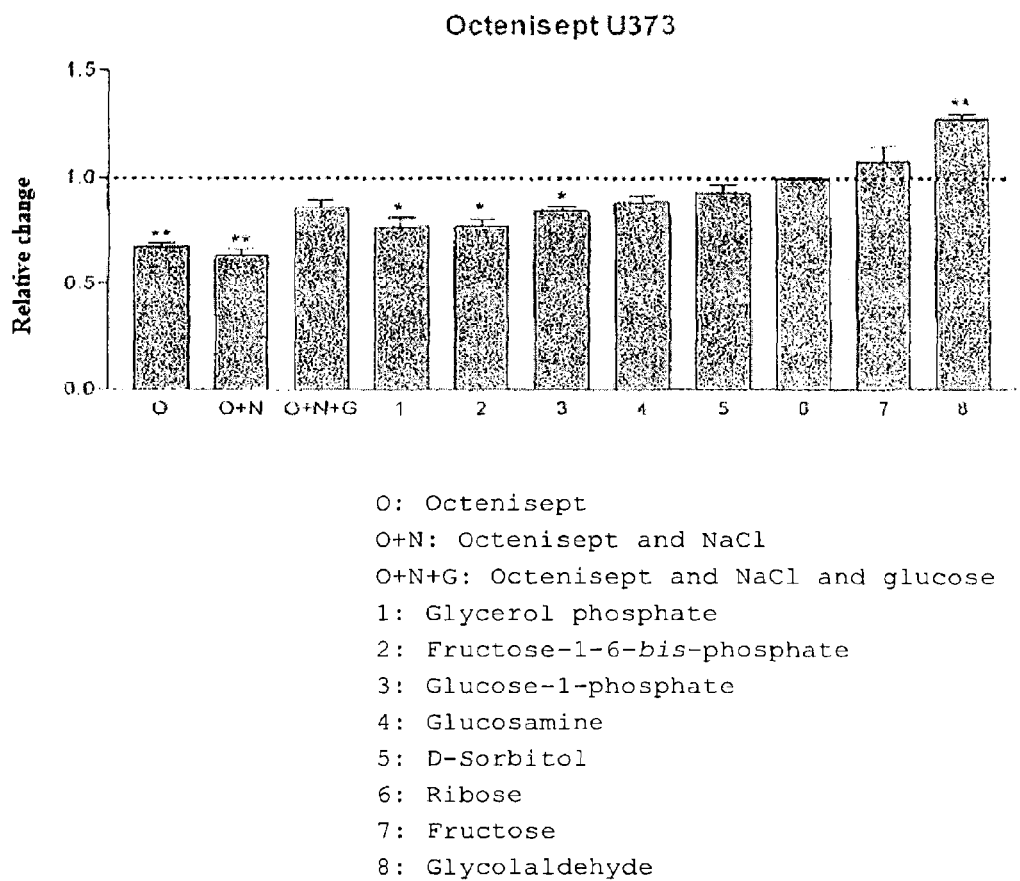

FIGS. 3a and 3b: Modification of the Octenisept® induced cell detachment through the addition of different carbohydrates in the cell detachment assay with Methyl violet.

Figure 4:
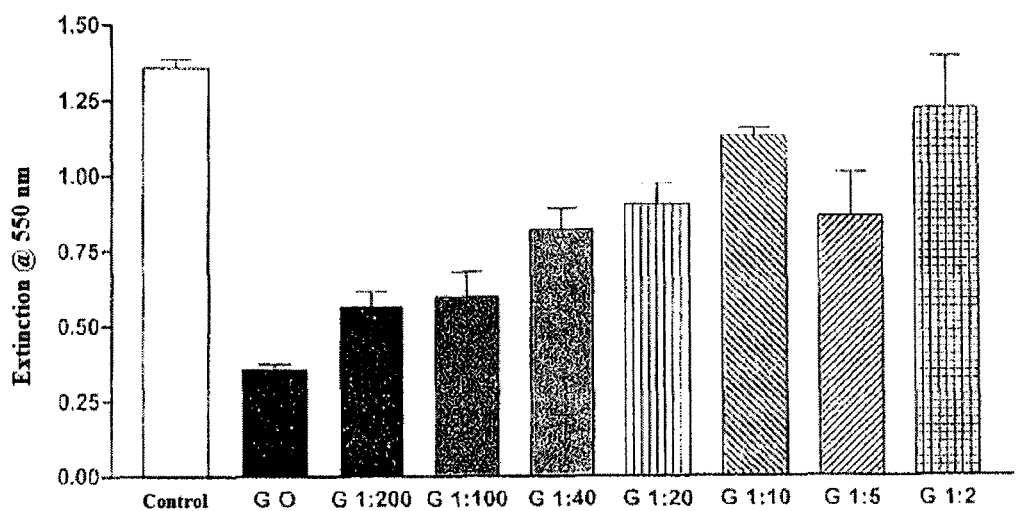

FIG. 4: Concentration dependency of glucose additives on the Octenisept® induced cell detachment from the culture media in the Methyl violet assay. After washing and staining of the adherent cells with Methyl violet the extinction was measured at 550 nm (the bars represent the mean value±standard deviation of 3 readings). The dilution is carried out beginning with a 0.1% octenidine solution (Octenisept®) with a 5% glucose solution in steps of between 0.01:200 to 1:2.

EXAMPLES

The ideal constellation for treating wounds is I. the superficial destruction of the microbial biofilm on the wound and II. the stimulation of those processes of the wound healing which lead to a solid coating of the underneath lying tissues. In the cell culture the anchoring of proliferating cells in the tissue structure corresponds with the formation of solid connections between the cytoskeleton, integrins and the matrix at the bottom of the culture dish. In order to quantify these parameters the resistance against the detachment of the cell layer is determined under mechanical stress like washing. The remaining cell layer is stained with Methyl violet and quantified through photometric absorptiometry. Additional effects which are achieved through the use of specific glucose solutions in defined dilutions with Octenisept® and which improve the cell adhesion and explain the observed improved wound healing are demonstrated.

Example 1

Reagents

Octenisept® (Schülke & Mayr) solution (0.1% (w/w) octenidine dihydrochloride and 2% (w/w) 2-phenoxyethanol in H$_2$O); NaCl solution (0.9% (w/v) in H$_2$O); glucose 5% (Mayrhofer Pharmaceuticals) glucose solution 5% (w/v) in H$_2$O;

Lactose, 2-deoxyglucose, saccharose, fructose, polyethylen glycol, chondroitin-4-sulfate, chondroitin-6-sulfate, dermatan sulfate and dextran sulfate were used sterilely filtered in a final concentration of 5% (w/v) in H$_2$O.

For the incubation with cell cultures equal parts of Octenisept® and the particular additives were mixed and stored at 4° C. for up to a week before usage.

Example 2

Cell Culture

The humane glioblastoma cell line U373 was cultured in Dulbecco's Modified Eagle Medium (DMEM) supplemented with 10% PCS (Gibco™), 2 mM glutamine (PPA) and 100 U/ml penicillin/streptomycin (PAA) at 37° and 5% CO$_2$. The cells were cultivated in monolayer and passaged at 80% confluence. Before carrying out the cell adhesion experiments the cells were transferred onto 96-well plates and brought to confluence.

Example 3

Determination of Cell Adhesion

Cell adhesion was carried out as described in detail in the quotation (Uchide, N. and Toyoda H., (2007) *J Immunol Methods*, 328 (1-2): 215-9). U373 cells were incubated in 96-well plates with Octenisept® (final concentration 5% (v/v) Octenisept®, this equates 0.005% octenidine dihydrochloride) alone or with the specified additives (5% v/v) for 1 hour in glucose-free Leibovitz medium. After removing the supernatant the standardized washing procedure was executed 3 times after which PBS was added with a motor-controlled pipet which led to the detachment of non-adhesive cells. Afterward only those cells whose matrix had formed a solid connection were fixed with glutaraldehyde and after removal of the glutaraldehyde stained with Methyl violet. The precipitated stain was dissolved with an SDS buffer and the extinction was measured at 550 nm in an ELISA plate reader.

Example 4

Precipitation Assay

The stability of the solubility of the components of Octenisept® in NaCl solution as an indicator for their interaction was determined through the analysis of the precipitates. After the co-incubation of Octenisept® with equal parts of 0.9% w/v NaCl or 5% carbohydrates in sterile aqua bidest for 3, 12, 24 and 72 hours at 4° C. the solutions were centrifuged at 2500 rpm for 5 minutes and the precipitate, if existing, was analyzed with the Zeiss inverted microscope with a digital camera with the METAVIEW micro-photography documentation system.

Example 5

Addition of NaCl to Octenisept® Leads to Crystallization and Precipitation

Positively charged octenidine and negative charges on the bacterial surface initiate its effectiveness. If one administers Octenisept® in a dilution of 1:1 with physiological sodium chloride solution like it is conventionally done a mixed hydrate shell consisting of NaCl and the dipole water will form around the octenidine molecule. The high ionic strength in solutions with NaCl$_{physiol}$ leads—without being limited to a specific theory—to a reduction of the bactericidal effect which is based on the positive charge of the octenidine. Hence, the dilution with NaCl impairs the effectiveness. It was now demonstrated that this not only constitutes a slight impairment but in particular also an induced crystallization. Micro-photography of the Crystalline Sediments:

A crystalline sediment (FIG. 1) develops in mixtures of Octenisept® with physiological sodium chloride solution after 96 hours of incubation at 4° C. which dissolves again when heated to 60° C. (20×lens). In mixtures of Octenisept® with 5% glucose (1:1) no sediment can be confirmed even after 30 days. Other polar uncharged carbohydrates as diluents do not form crystals, however, sulfated polymeric hydrocarbons like chondroitin sulfate, dermatan sulfate or heparan sulfate which lead to a quick micro-crystalline or colloidal turbidity do.

Example 6

Effects of Glucose and NaCl Additives on Octenisept® Induced Cell Adhesion from the Culture Media in a Methyl Violet Assay The crystalline sediment can be prevented through dilutions with 5% glucose solution. It was now examined whether this additive ensures effects which can contribute to the improvement of wound healing. U373 cells were incubated for 1 hour in Leibovitz medium with Octenisept® alone or with additives (1:1 with glucose 5% or NaCl 0.9%). In each case 5 µl of the respective solution was added to 100 µl of medium. After washing and staining of the adherent cells with crystal violet the extinction was measured at 550 nm (FIG. 2$a$). The extinction of the controls was set to 1. Statistical significances were determined with Bonferroni's Multiple Comparison Test (: $p<0.01$, *$<0.001$).

Cells which were treated with Octenisept® alone (black bars) showed a stability reduced to 50% compared with cultures in the Leibovitz medium, which was further reduced through dilution with NaCl 0.9% (vertically striped bars). With glucose 5% the resistance against detachment was very significantly improved to 80% of the control value (gray bars). A concentration series with glucose revealed that the optimal addition is 2% in the stock solution or 0.1% final concentration (FIG. 4). The number of cells which adhered to the substrate after the treatment with Octenisept®+glucose was significantly higher than after treatment with Octenisept®+NaCl wherein at the highest concentration of Octenisept®+NaCl all cells were detached while Octenisept®+glucose achieved a more solid anchoring which allowed keeping an intact cell layer (FIG. 2$b$).

Example 7

Modification of Octenisept® Induced Cell Adhesion Through Different Polyalcohols Polyalcohols form a broad compound class and it was therefore examined whether single subgroups have different effects in the adhesion test. U373 cells were incubated in Leibovitz medium with 5 µl additive to 100 µl medium in each case for 1 hour with Octenisept® alone (−) or with additives (1:1 with polyalcohol 5%, glucose, 2-deoxyglucose (2-deoxyG.), lactose, saccharose, fructose, glucuronic acid, polyethylene glycol (PEG), chondroitin-4-sulfate (ch.4-s.), chondroitin-6-sulfate (ch.-6-s.) dermatan sulfate (dermatan-s.) or dextran sulfate (dextran-s.)). After washing and staining of the adherent cells with Methyl violet the extinction was measured at 550 nm. (Bars represent the mean value±SD of two independent experiments (measured in triplicates)). The extinction of the controls was set to 1. Statistical significances were determined with Bonferroni's Multiple Comparison Test (: p<0.01, *<0.001).

FIG. 3 shows that Octenisept® on the other hand led to a significant reduction of the cell adhesion which was again improved through polar monomers like glucose, 2-deoxyglucose, fructose and glucuronic acid but also through disaccharides like lactose, saccharose and polymers with polyethylene glycol. Charged polymers like chondroitin-4-sulfate, chondroitin-6-sulfate, dermatan sulfate and dextran sulfate could not achieve this effect but significantly reduced the adhesion to under the values of NaCl.

The effectiveness of polyalcohols as additives to octenidine was verified in experiments for uncharged or slightly acid carbohydrates. The tested polymeric sulfated carbohydrates, however, had no effect. In detail aldohexoses and aldopentoses act equivalently positive and there is no difference between aldoses and ketoses in this class. In derivatives without aldehyde groups a slight reduction of the positive effect has to be recorded (sugar alcohols, PEG). Glycosidic OH groups can be bound without impairing the effect like it is shown with saccharose as an example. Instead acid groups rather seem to play a role when it comes to binding cations. Glucuronic acid as internal ester therefore has a positive effect but phosphate or sulfate derivatized carbohydrates do not since they furthermore intensify the octenidine induced detachment of the cells. These findings are congruent with the antiseptic hypothesis of effectiveness insofar as a reduced bactericidal effect was deduced through a charge balancing, like it is achieved through strong halogens. The use of carbohydrates reduces the physiological sodium chloride concentration during the application and supports the already well documented antiseptic effect.

Example 8

Concentration Dependency of Glucose Additives on Octenisept® Induced Cell Adhesion from the Culture Media in a Methyl Violet Assay In order to determine the optimal concentration or dilution at which the preparation with glucose additive re-balances the cell adhesion, which is significantly reduced through Octenisept® alone or Octenisept® diluted with NaCl, a dilution series of the preparations with glucose 5% of 1:2 to 1:200 was used. U373 cells were incubated for one hour with Octenisept® (1:20 in medium) alone (G0) or with Octenisept® and different volumes of a 5% glucose solution (resulting final dilution 1:200-1:2 in Leibovitz medium). The effects on the cell adhesion were determined through the Methyl violet test and are demonstrated in FIG. 4.

Octenisept® causes a substantial reduction of the cell adherence which was tendentially improved through the addition of glucose 1:200 or 1:100. The optimum of the protective effect was determined at a dilution of 1:20 and shows in case of further increasing concentrations significant variations but no constant and substantially enhanced protective effect.

An Experiment on cell cultures could prove: The number of cells adherent to the substrate after a standardized washing process was after the treatment with Octenisept®+glucose significantly higher than after the treatment with Octenisept®+NaCl, wherein at the highest concentration of Octenisept®+NaCl all cells were detached while Octenisept®+glucose achieved a more solid anchoring. Analogously to the wound healing in vivo this parameter indicates that a dilution of Octenisept®+glucose supports the manufacture of a mechanically solid cell structure and therefore accelerates the wound healing (Cai et al., (2008) *Invest Ophthalmol Vis Sei,* 49(5): 2163-71; Chiang et al., (1991) *Dev Biol,* 146(2): 377-85; Guo et al., (2008) *Cancer Investigation,* 26(4): 369-374; Wilkinson et al., (1994) *Exp Dermatol,* 3(5): 239-45). The optimal range of use was determined at a dilution of 1:20 of the 5% glucose solution or 0.25% absolute glucose in the Octenisept solution.

The invention claimed is:

1. A solution, comprising:
    octenidine or a pharmaceutical salt thereof; and
    a polyalcohol of formula 2: $C_n(H_2O)_m$, wherein n is an integer of at least 3 and m is an integer in a range of n−15% to n+15% as a rounded integer
    and wherein the polyalcohol is a cyclic acetal or cyclic ketal and the polyalcohol comprises a carboxylic acid group.

2. A kit comprising the solution of claim 1.

3. A pharmaceutical composition, comprising the solution of claim 1.

4. The solution of claim 1, wherein the polyalcohol is glucuronic acid.

5. The solution of claim 1, wherein the polyalcohol is a mono-carboxylic acid derivative of a mono- or disaccharide.

6. The solution of claim 1, wherein a concentration of the polyalcohol is between 0.01% to 12% (w/v), based on the volume of the solution.

7. The solution of claim 1, wherein a concentration of the octenidine is between 0.0001% to 1% (w/w), based on the weight of the solution.

8. The solution of claim 1,
    wherein a NaCl concentration is under 0.1% (w/v), based on the volume of the solution.

9. A wound dressing or a swab, comprising the solution of claim 1.

10. A pharmaceutical agent, comprising a solution comprising:
    octenidine or one of its pharmaceutically acceptable salts; and
    glucuronic acid,
    with a glucuronic acid concentration of between 0.01% to 12% (w/v), and an octenidine concentration of between 0.0001% to 1% (w/w),
    optionally in combination with a carrier.

11. The solution of claim 1, comprising a pharmaceutical salt of octenidine wherein the pharmaceutical salt is octenidine dihydrochloride.

* * * * *